United States Patent [19]
Evers et al.

[11] Patent Number: 5,817,044
[45] Date of Patent: Oct. 6, 1998

[54] USER ACTIVATED IONTOPHOERTIC DEVICE

[75] Inventors: Hans Christer Arvid Evers, Södertälje; Bernt Fredrick Julius Broberg, Trosa, both of Sweden; John D. DeNuzzio, Chapel Hill; Randal A. Hoke, Cary, both of N.C.

[73] Assignee: Becton Dickenson and Company, Franklin Lakes, N.J.

[21] Appl. No.: 282,100

[22] Filed: Jul. 28, 1994

Related U.S. Application Data

[63] Continuation of Ser. No. 972,280, Nov. 5, 1992, abandoned.

[51] Int. Cl.[6] .................................................. A61N 1/30
[52] U.S. Cl. ........................... 604/20; 604/307; 604/306; 607/153
[58] Field of Search ............................ 604/20, 306, 307; 607/153

[56] References Cited

U.S. PATENT DOCUMENTS

| | | | |
|---|---|---|---|
| 3,814,095 | 6/1974 | Lubens | 128/260 |
| 4,474,570 | 10/1984 | Ariura et al. | 604/20 |
| 4,666,441 | 5/1987 | Andriola | 424/449 |
| 4,693,711 | 9/1987 | Bremer et al. | 604/306 |
| 4,722,726 | 2/1988 | Sanderson et al. | 604/20 |
| 4,820,263 | 4/1989 | Spevak et al. | 604/20 |
| 4,842,577 | 6/1989 | Konno et al. | 604/20 |
| 4,911,707 | 3/1990 | Heiber et al. | 424/449 |
| 4,917,676 | 4/1990 | Heiber et al. | 424/449 |
| 4,919,648 | 4/1990 | Sibalis | 604/20 |
| 4,921,475 | 5/1990 | Sibalis | 604/20 |
| 4,927,408 | 5/1990 | Haak et al. | 128/798 |
| 4,994,023 | 2/1991 | Wellinghoff et al. | 604/20 |
| 5,053,001 | 10/1991 | Reller et al. | 604/20 |
| 5,077,033 | 12/1991 | Viegas et al. | 514/716 |
| 5,084,008 | 1/1992 | Phipps | 604/20 |
| 5,087,240 | 2/1992 | Sibalis | 604/20 |
| 5,087,242 | 2/1992 | Petelenz et al. | 604/20 |
| 5,125,894 | 6/1992 | Phipps et al. | 604/20 |
| 5,128,137 | 7/1992 | Muller et al. | 424/449 |
| 5,158,537 | 10/1992 | Haak et al. | 128/803 |
| 5,250,022 | 10/1993 | Chein et al. | 607/153 |
| 5,288,289 | 2/1994 | Haak et al. | 604/20 |
| 5,310,404 | 5/1994 | Gyory et al. | 604/20 |
| 5,320,598 | 6/1994 | Haak et al. | 604/20 |
| 5,385,543 | 1/1995 | Haak et al. | 604/20 |

FOREIGN PATENT DOCUMENTS

| | | |
|---|---|---|
| 0060451 | 9/1982 | European Pat. Off. . |
| 0151953 | 8/1985 | European Pat. Off. . |
| 4040911 | 6/1991 | Germany . |
| 2160427 | 12/1985 | United Kingdom .................. 128/802 |
| WO91/03998 | 4/1991 | WIPO . |
| WO91/15260 | 10/1991 | WIPO . |
| WO91/15261 | 10/1991 | WIPO . |
| WO92/07618 | 5/1992 | WIPO . |
| WO92/07619 | 5/1992 | WIPO . |
| WO92/10235 | 6/1992 | WIPO . |

OTHER PUBLICATIONS

Sterile Dosage Forms, Turco & King published 1974 p. 177, lines 24–40.

*Primary Examiner*—Paul B. Prebilic
*Attorney, Agent, or Firm*—Susan A. Capello; Arthur D. Dawson

[57] ABSTRACT

A user activated iontophoretic device of the present invention includes an electrode assembly, an electrode reservoir and at least one drug reservoir. The device is divided or otherwise separated into at least two portions, with one portion containing the electrode reservoir and the other containing the drug reservoir, which may include a medication in a dry form. In one embodiment, the two portions are each contained in separate compartments of a pouch. In another embodiment, the portions are contained in a single compartment and divided by a barrier. A method of activating the device includes causing the two portions to come into electrical conducting contact with one another to at least partially hydrate one of the reservoirs. This can be accomplished, for example, by either folding the device to bring the two portions into contact with one another or simply by removing the barrier dividing the two portions. In the alternative, the device may include two separate portions which can be brought together to activate the device. In this way, the device is suitable for use to deliver a high dose efficiency, while providing a commercially suitable shelf-life.

11 Claims, 5 Drawing Sheets

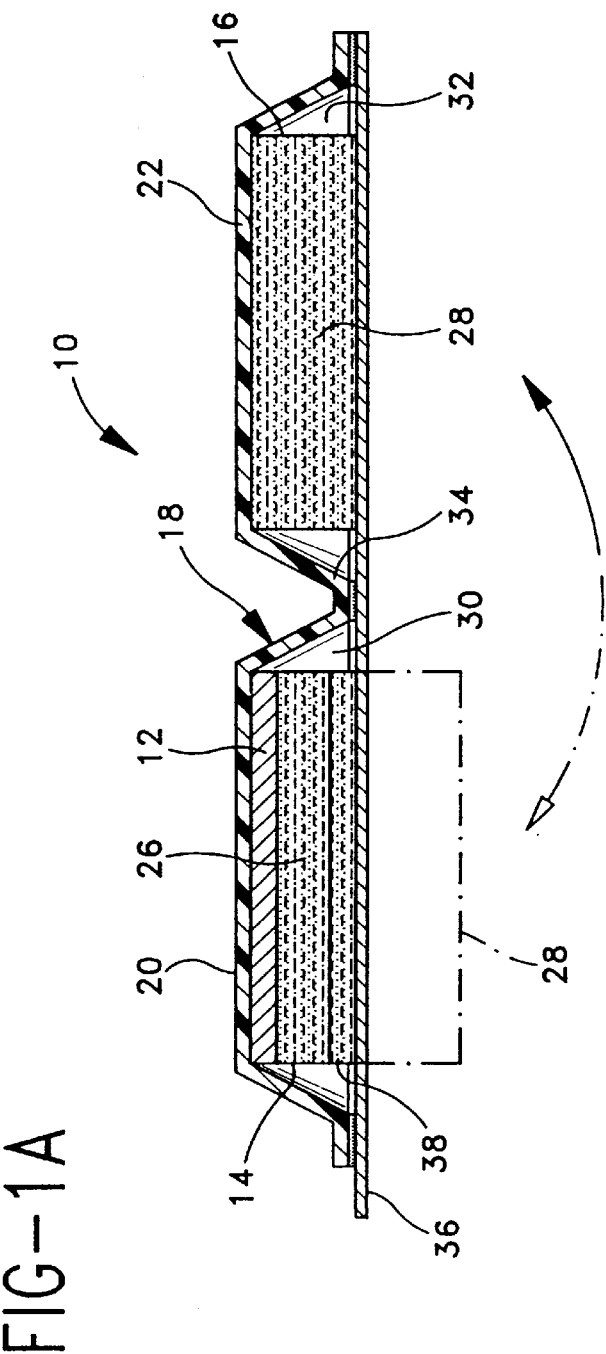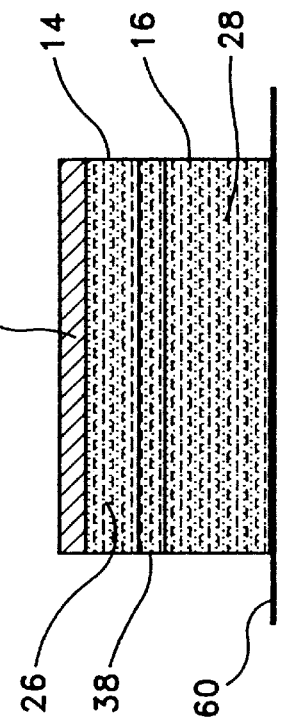

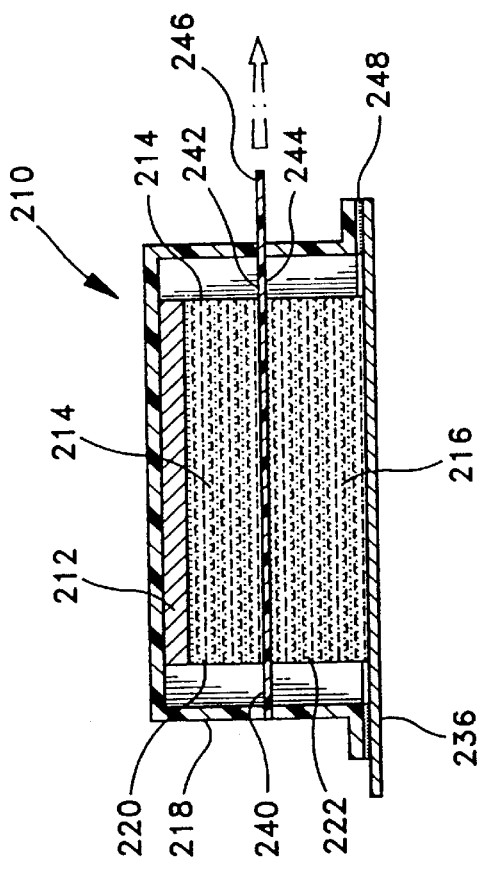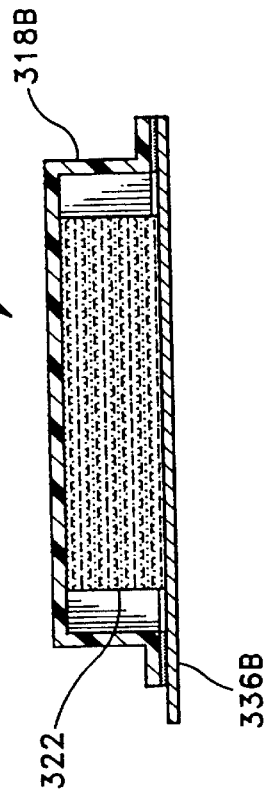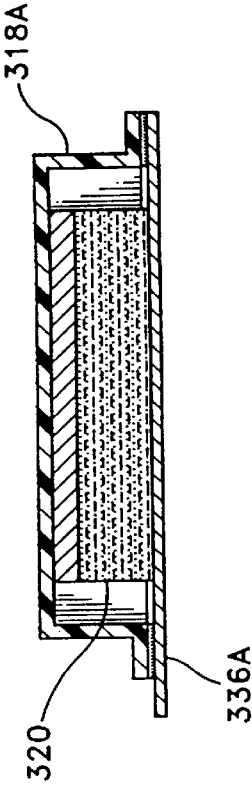

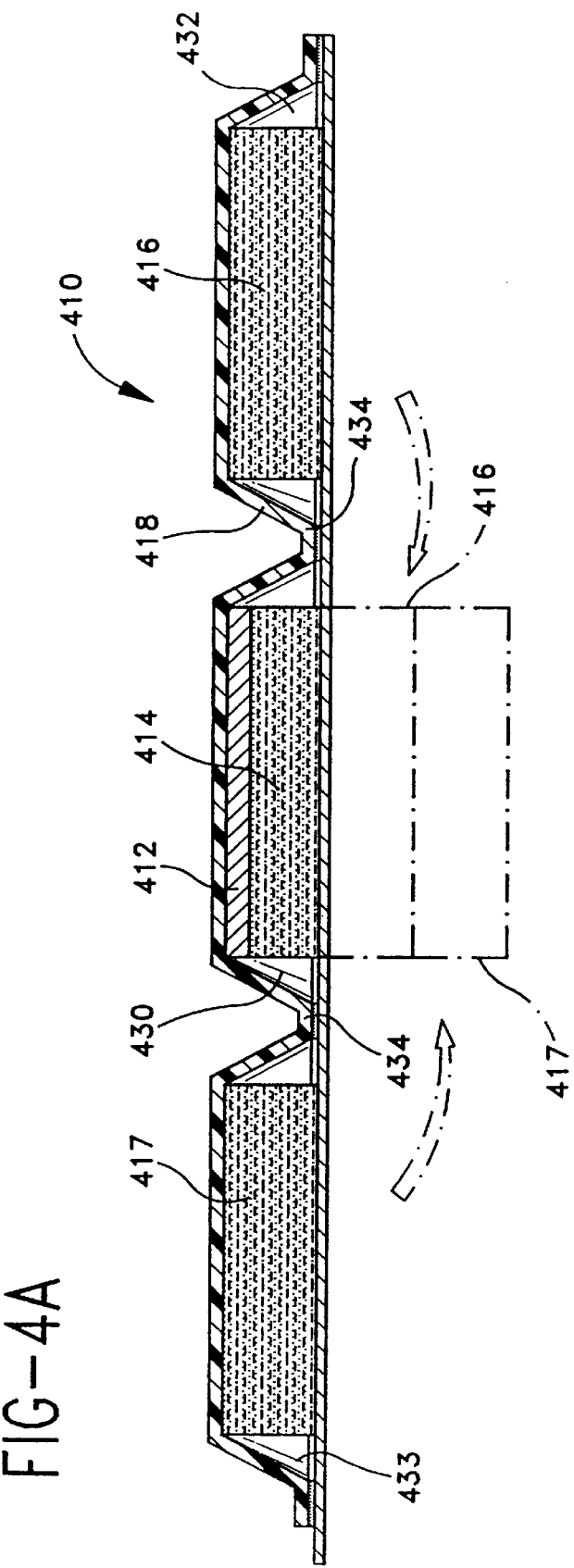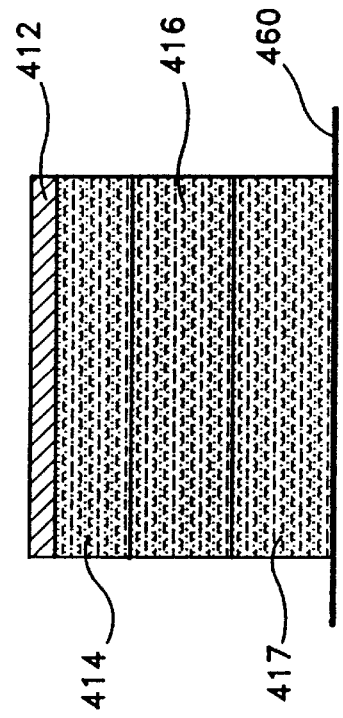

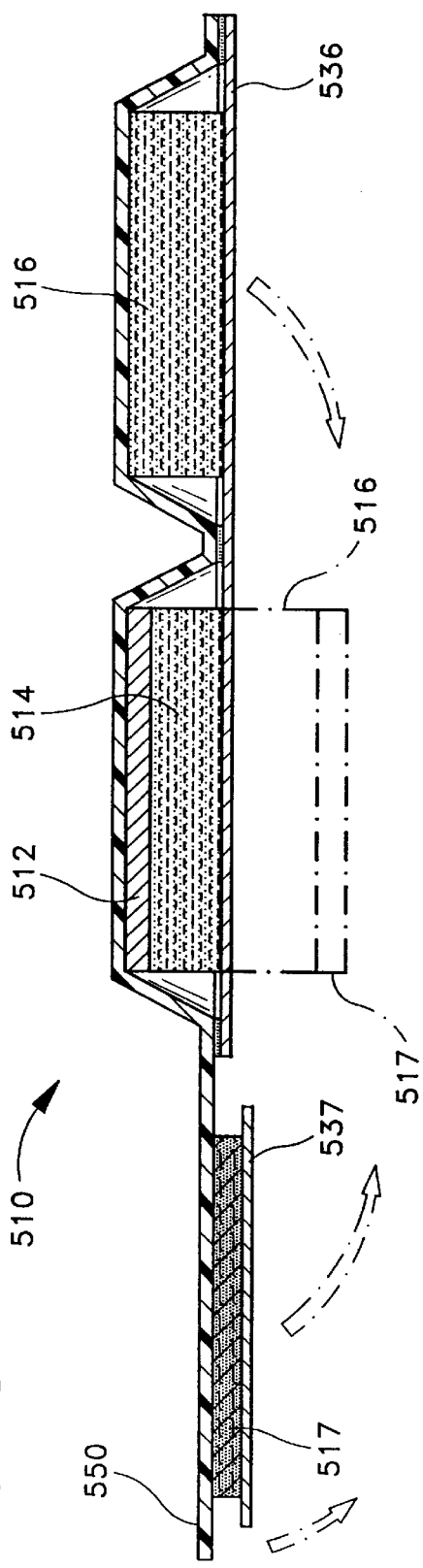
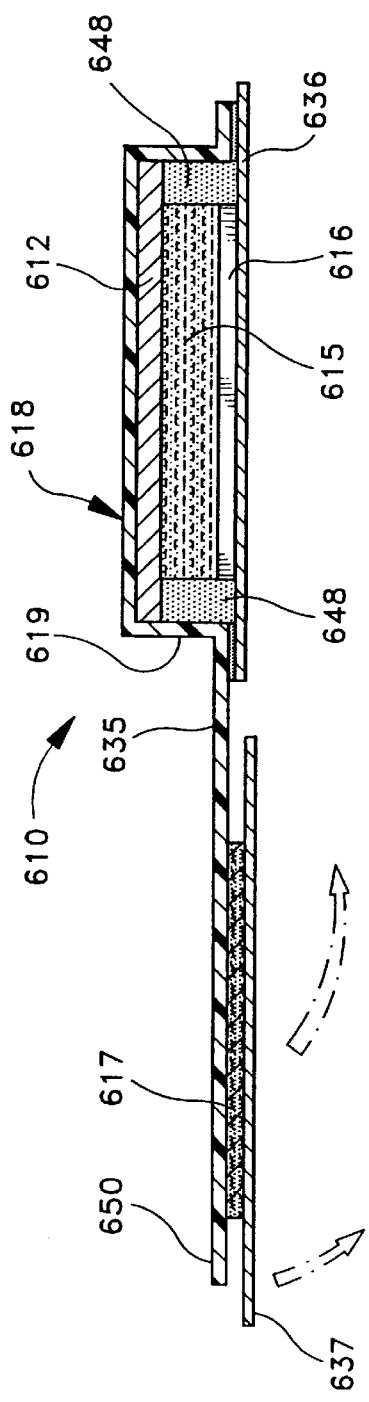

USER ACTIVATED IONTOPHOERTIC DEVICE

This application is a continuation of application Ser. No. 07/972,280, filed Nov. 5, 1992 now abandoned.

FIELD OF THE INVENTION

The present invention generally relates to iontophoretic devices for delivering drugs or medicines to patients transdermally, i.e., through the skin, and more specifically relates to an iontophoretic device and method capable of being activated by the user.

BACKGROUND OF THE INVENTION

Transdermal drug delivery systems have, in recent years, become an increasingly important means of administering drugs. Such systems offer advantages clearly not achievable by other modes of administration such as avoiding introduction of the drug through the gastrointestinal tract or punctures in the skin to name a few.

Presently, there are two types of transdermal drug delivery systems, i.e., "Passive" and "Active." Passive systems deliver drug through the skin of the user unaided, an example of which would involve the application of a topical anesthetic to provide localized relief, as disclosed in U.S. Pat. No. 3,814,095 (Lubens). Active systems on the other hand deliver drug through the skin of the user using iontophoresis, which according to *Stedman's Medical Dictionary*, is defined as "the introduction into the tissues, by means of an electric current, of the ions of a chosen medicament."

Conventional iontophoretic devices, such as those described in U.S. Pat. Nos. 4,820,263 (Spevak et al.), 4,927,408 (Haak et al.) and 5,084,008 (Phipps), the disclosures of which are hereby incorporated by reference, for delivering a drug or medicine transdermally through iontophoresis, basically consist of two electrodes—an anode and a cathode. Usually, electric current is driven from an external supply into the skin at the anode, and back out at the cathode. Accordingly, there has been considerable interest in iontophoresis to perform delivery of drugs for a variety of purposes. Two such examples, involve the use of procaine, which is usually injected prior to dental work to relieve pain, and lidocaine, which is usually applied as a topical, local anesthetic.

However, several disadvantages and limitations have been associated with the use of such devices, including storage stability as a result of the drug not being in a form suitably stable to provide a commercially practical shelf life. Upon storage for extended periods, the therapeutic agents can degrade and become less potent. In addition, such devices have not delivered an efficient dosage of the drug resulting in poor performance and a need for larger amounts of the drug, which upon completion of the application is wasted. Accordingly, such devices have been generally impractical for use on outpatients and in doctor's offices, since the products do not have sufficient shelf life and neither the patient nor the practitioner wishes to wait the required time for the desired effect.

Several of the prior passive type devices have attempted to overcome or minimize one such limitation, i.e., shelf life, by including a "burstable" member to isolate or separate the drug as disclosed in U.S. Pat. Nos. 4,911,707 (Heiber et al.) and 4,917,676 (Heiber et al.). However, limitations remain with respect to the use of such devices, particularly when "bursting" the member. During this event, the drug would be mixed with the activating solution limiting the dose efficiency of the device.

Another attempt to overcome this problem has included adding the drug to the device prior to use as disclosed, for example, in U.S. Pat. No. 4,722,726 (Sanderson et al.), by injecting the drug into a chamber. However, other limitations remain with respect to the use of such devices, particularly when injecting the drug. During this event, the device is difficult to use, especially by persons who are handicapped or infirmed by some disability or limitation. In addition, such devices have not provided an efficient dosage as a result of the presence of competing ions.

Attempts to provide dose efficient devices have included two-compartment configurations, such as those described in the patents to Haak et al. and Phipps, separating the drug to be administered from the electrolytic solution. However, such devices have failed to address the need for long-term stability and shelf-life to prevent degradation of the drug. Also, slow transport and equilibration between the compartments can dilute the drug formulation, thus decreasing the dose efficiency of the device.

Thus, there has been a need for a user activated iontophoretic device, which would eliminate the problems and limitations associated with the prior devices discussed above, most significant of the problems being associated with storage of the device, i.e., shelf-life, and dose efficiency.

SUMMARY OF THE INVENTION

In contrast to the prior devices discussed above, it has been found that a iontophoretic device particularly suited for use to deliver a high dose efficiency, while providing a commercially suitable shelf-life can be constructed in accordance with the present invention. In addition, the device of the present invention is easily activated by the user to administer the drug. Such users may include the patient as well as doctors, nurses and the like.

The user activated device for delivering at least one medication to an applied area of a patient, such as the skin, mucus membrane and the like, of the present invention includes electrode assembly means for driving a medication into the applied area of the patient to be absorbed by the body of the patient, a first reservoir situated in relation to the electrode assembly means and a second reservoir containing a medication to be delivered to the applied area of the patient and holding means for holding the electrode assembly means, the first reservoir and the second reservoir. The holding means includes first means for maintaining the electrode assembly means in electrical communication with the first reservoir and second means for maintaining the second reservoir separate in relation to the first reservoir prior to activation such as to prevent degradation and dilution of the medication contained in the second reservoir and upon activation the first reservoir and the second reservoir are brought into contact with one another to at least partially hydrate one of the reservoirs, thus increasing the dose efficiency of the device, while permitting electrical conducting contact between the first reservoir and the second reservoir after activation. The medication contained in the second reservoir is maintained in a dry state prior to activation. In addition, the first reservoir may include a second medication to be delivered to the applied area of the patient.

In the preferred embodiment, the first means and the second means are hingedly connected together along a bendable member so that the device may be activated by folding the holding means along the bendable member to bring the first reservoir and the second reservoir into electrical conducting contact with one another.

In an alternative embodiment, the device also includes barrier means for separating the first reservoir from the second reservoir, which may be manipulated to bring the first reservoir and the second reservoir into electrical conducting contact with one another. In this embodiment, the barrier means is adapted to include an upper release surface, a lower release surface and a pull tab extending from the holding means so that the device may be activated by pulling the tab to remove the barrier from the device.

The method of iontophoretically delivering at least one medication through an applied area of a patient such as the skin, mucus membrane or the like, includes exposing a first portion of a device including an electrode assembly and a first reservoir and exposing a second portion of the device including a second reservoir containing a medication to be delivered to the patient separate from the first portion. The first reservoir of the first portion of the device is brought into electrical conducting contact with the second reservoir of the second portion of the device to at least partially hydrate one of the reservoirs and to form a combined portion, with the combined portion of the device applied to an area of the patient to be treated. In addition, current is caused to flow through the device into the applied area to drive the medication into the body of the patient.

In an alternative embodiment, a hydrating solution is applied to the area of the patient prior to activation of the device and application of the device onto the applied area of the patient.

The user activated iontophoretic device for delivering at least one medication through an applied area of a patient, such as the skin, mucus membrane and the like, of the present invention includes a first portion and a second portion. The first portion includes an electrode assembly and a first reservoir, and the second portion includes a second reservoir. The electrode assembly includes electrode means for driving a medication into the patient to be absorbed by the body of the patient. The first reservoir which is electrically conductive contains an active compound to be delivered to the applied area of the patient, and the second reservoir contains a vasoactive agent to be delivered to the applied area of the patient. In addition, holding means holds the first portion and the second portion separate from one another, with the electrode assembly maintained in electrically communicating relation with the first reservoir, and with the vasoactive agent contained by the second reservoir maintained separate in relation to the first portion prior to activation. In this way, upon activation, the first reservoir and the second reservoir may be brought into electrical conducting contact with one another and at least of the reservoirs is at least partially hydrated.

In addition, upon activation, the vasoactive agent may be dissolved at the interface of the two reservoirs, with the vasoactive agent in contact with the applied area of the patient. Also, the vasoactive agent may be initially in a dry form separated from the active compound with the holding means sealed to keep the first portion intact during storage. Also, the active compound may include a local anaesthetic such as lidocaine, and the vasoactive agent may include a vasoconstricting compound such as adrenaline.

BRIEF DESCRIPTION OF THE DRAWINGS

The various features, objects, benefits, and advantages of the present invention will become more apparent upon reading the following detailed description of the preferred embodiment along with the appended claims in conjunction with the drawings, wherein like reference numerals identify corresponding components, and:

FIGS. 1A & 1B are schematic, cross sectional views of one embodiment of the user activated iontophoretic device of the present invention, with FIG. 1A illustrating the device prior to activation and FIG. 1B illustrating the device after activation;

FIG. 2 is a schematic, cross sectional view of another embodiment of the device of the present invention illustrated prior to activation;

FIGS. 3A & 3B are schematic, cross sectional views of yet another embodiment of the device of the present invention illustrated prior to activation;

FIGS. 4A & 4B are schematic, cross sectional views of another embodiment of the device of the present invention including a second drug reservoir and illustrated prior to and after activation;

FIG. 5 is a schematic, cross sectional view of another embodiment the device illustrated prior to activation; and FIGS. 6A, 6B & 6C are schematic views of yet another embodiment of the device of the present invention, with FIG. 6A being a cross sectional view illustrating the device prior to activation, FIG. 6B being a bottom view illustrating the device prior to activation, and FIG. 6C being a cross section side view illustrating the device after activation.

DETAILED DESCRIPTION OF THE PREFERRED EMBODIMENT

Figure 6B:
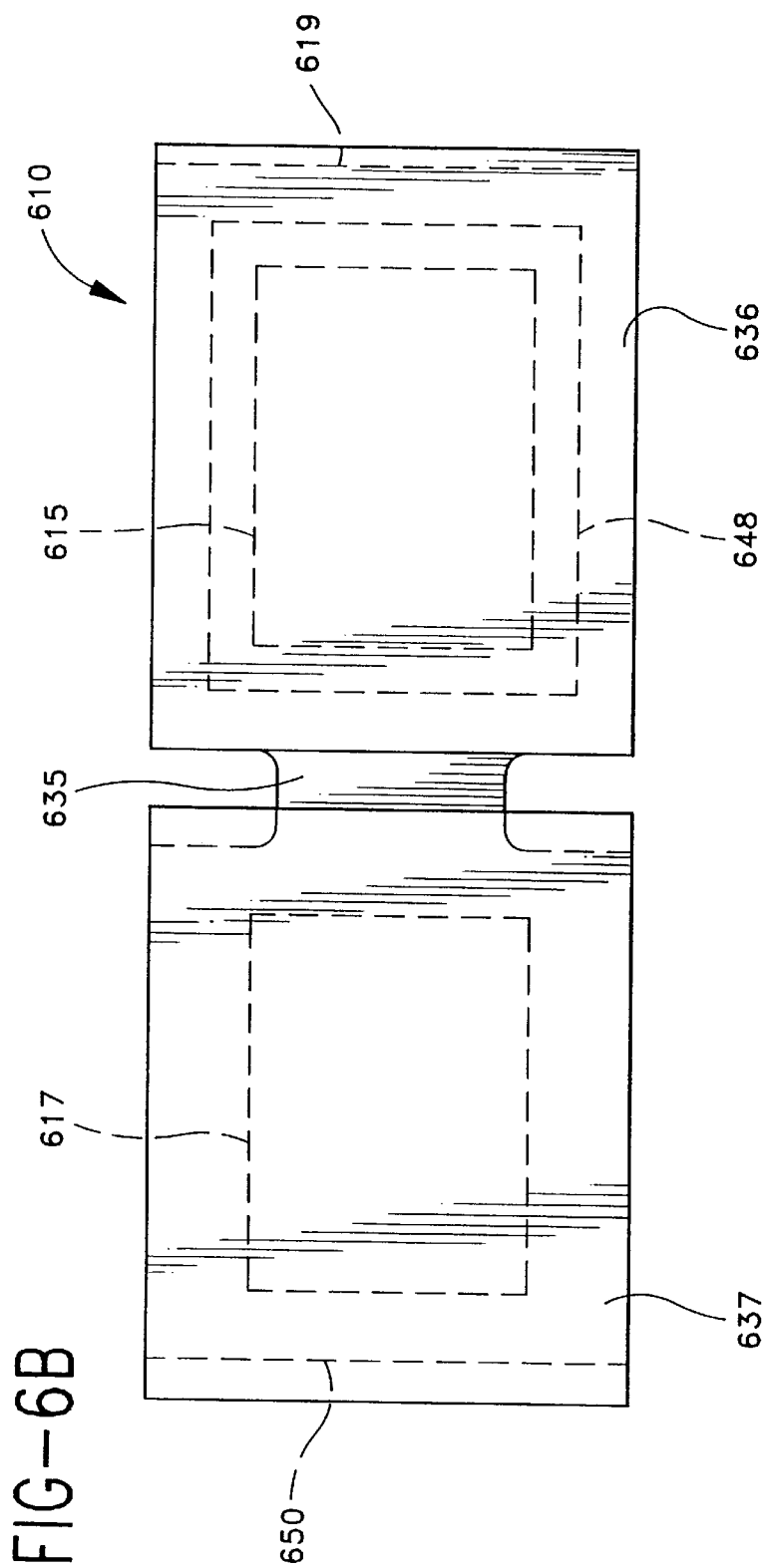

The user activated iontophoretic device of the present invention is illustrated in FIGS. 1–6 and generally includes the designation 10. Referring to FIGS. 1A and 1B, the device or patch 10 of the present invention includes an electrode assembly 12, having at least one electrode, an electrode reservoir 14 and at least one drug reservoir 16, which are held or contained within a pouch or other suitable structure 18. It should be appreciated that a return electrode may be combined in the assembly 12 or separately provided as is well known in the art.

In the preferred embodiment, the device is divided or otherwise separated into two portions, one portion 20 (first) includes the electrode assembly 12 and the electrode reservoir 14 with the electrode reservoir being situated adjacent to the electrode assembly and holding an electrolyte 26. The other portion 22 (second) includes the drug reservoir 16 which holds the medication or drug 28, preferably in an ionized or ionizable form, to be delivered iontophoretically. The particular electrolyte is not essential to the present invention and is merely a matter of choice. However, in this embodiment the electrolyte may include sodium chloride in an aqueous solution, gel matrix or the like.

The pouch 18 has at least two compartments 30, 32, with one compartment 30 (first) containing the first portion 20 of the device and the second compartment 32 containing the other portion 22 (second). The two compartments 30, 32 are hingedly connected together along a bendable member 34 with a release liner 36 sealing the two compartments. In this way, the drug can be stored or otherwise isolated from the first portion, in a dry state or formulation in a matrix or on a supporting substrate, which can be hydrated prior to use. Also, the drug can be stored in a non-aqueous solvent such as low molecular weight polyethylene glycol or glycerine. The drug may be stable in such non-aqueous solvents, and the solution (with the ionized or ionizable drug) may be an adequate electrolyte depending upon the particular drug or combination of drugs. These solvents might also be used as humectants in a gel matrix.

At least one barrier 38 may be situated between the electrode reservoir 14 or the drug reservoir 16, either adjacent to the one or the other, to limit transport of ions between the two reservoirs when the two portions are caused to come into electrical conducting contact with one another as illustrated in FIG. 1B. The particular barrier used in this embodiment is not essential to the present invention and may include any of the membranes or forms described in the patents to Haak et al. and Phipps, depending upon the particular therapeutic application.

In the preferred embodiment, the two portions are brought into contact with one another by first removing the release liner 36 to expose the two portions 20, 22 and folding or otherwise bending the device along the bendable member to bring the two portions into contact with one another. In the alternative, the bendable member 34 may be a break-away or perforated member to permit the two compartments to be physically separated and then brought into contact with one another.

As is well known within the field, the device can then be applied to the patient and a voltage impressed across the electrodes of the electrode assembly 12 to cause current to flow through the skin 60 of the patient to drive the ionic medication into the skin and the tissue to be absorbed by the body of the patient. It should also be appreciated that the device of the present invention can be applied to other areas of the body such as mucus membranes depending upon the desired therapy and drugs to be delivered.

Another embodiment of the device of the present invention is illustrated in FIG. 2, and is generally designated 210 with the two portions 220, 222 of the device contained in a single structure 218 and separated by a barrier 240. The barrier 240 includes an upper release surface 242, a lower release surface 244 and a pull tab 246 extending from the structure. The release surfaces are provided to prevent the barrier from adhering to the adjacent portions of the device such as the reservoirs 214, 216.

The device 210 may also include a layer of adhesive 248 for adhering the device to the skin of the patient. However, prior to applying the device to the patient, the barrier 240 is removed by pulling the tab 246 to remove the barrier from the device and cause the electrode reservoir 214 and the drug reservoir 216 to come into electrical conducting contact with one another.

It should be appreciated that other forms of barriers may be used as long as they separate the two reservoirs 214, 216 of the two portions prior to application to prevent degradation of the drug through, for example, slow transport or equilibration between the reservoirs, or through other action which would otherwise result in the drug formulation being diluted, thus decreasing the dose efficiency of the device, while permitting electrical conducting contact between the reservoirs after activation. In this embodiment, the barrier is a vapor/liquid impermeable barrier which may be manipulated by being removed to activate the device.

Yet another embodiment of the device of present invention is illustrated in FIG. 3, and includes two separate parts, 310A and 310B contained in separate structures 318A and 318B, with the first part having a first portion 320 and the second part having a second portion 322, which after removal of the release liners 336A and 336B from each may be brought into contact with one another. This embodiment may be preferred for use in situation where the first portion 320 is a common or universal element and the second portion 322 is selected for use depending upon the drug or medicant contained therein and the desired therapy/treatment to be given to the patient. In this way, the first portion 320 may be used with different second portions 322 manufactured or otherwise produced with various drugs.

In the embodiment illustrated in FIGS. 4A and 4B, the device is generally designated 410 and includes a pouch or suitable structure 418 having three compartments 430, 432, 433, each separated by a bendable member 434. The first compartment 430 contains the electrode assembly 412, electrode reservoir 414, the second compartment contains the drug reservoir 416 and the third compartment contains a second drug reservoir 417 which is brought into contact with the skin 460 of the patient.

In the alternative, as illustrated in FIG. 5, the third portion of the device 510 may include a flexible member 550 upon which the second drug reservoir 517 may be attached. In this embodiment, the flexible member 550 simply includes the existing release liner 536 and a second release liner 537 with the second drug reservoir 517 sandwiched therebetween.

Figure 6C:
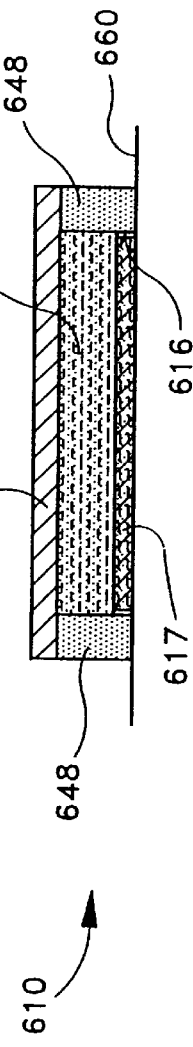

An alternative embodiment is illustrated in FIGS. 6A, 6B and 6C, and generally designated as 610. The device includes the electrode assembly 612, a first reservoir 615 combining the electrode reservoir and the first drug reservoir, and a second reservoir 617. These elements are contained within the structure 618 and covered by a backing or covering 619.

The first portion consists of the electrode assembly 612 and the first reservoir 615, and a space 616 for accommodating the second reservoir 617 within the structure with the second portion simply consisting of the second reservoir 617. The layer of adhesive 648 surrounds at least a portion of the first reservoir with the release liner 636 covering the exposed surfaces of both.

The second reservoir 617 is attached on one side to the flexible member 650 and on the other side to a second release liner 637, with the second reservoir sandwiched therebetween. The bendable member 635 hingedly connects the flexible member 650 to the backing 619 of the structure 618. In this embodiment, the backing preferably includes a foil material, which, e.g., may be plastic-laminated aluminum.

The first reservoir 615 of the device 610 can be electrically conductive and pre-assembled in electrical conducting contact with the electrode assembly 612, and prior to activation the second reservoir 617 can be brought into electrical conducting contact with the first reservoir along their interface. In this way, the first reservoir 615 can be used to contain a gel with an active compound such a local anaesthetic, e.g., lidocaine, dispersed therein, and the second reservoir 617 can be used to contain a vasoactive agent such as adrenaline. The addition of the vasoactive agent provides additional localization of the local anaesthetic agent at the applied area by being vasoconstricting, which has been found to significantly increase both the depth or magnitude of dermal analgesia and prolongation of the duration of the desired effect.

Upon activation, the vasoactive agent may be dissolved at the interface of the reservoirs, due to its solubility in an aqueous fluid. Thus, after attaching the device to a suitable area of the skin 660 of the patient, with the vasoactive agent in contact with the skin, current can be applied. The local anaesthetic agent and the active compound act together during the iontophoretic administration period.

Due to oxidation and hydrolysis of the in aqueous solutions instable substances, such as adrenaline, during storage at normal, that is room temperatures, it has been found that the activity of the vasoactive substance as a vasoconstrictor is decreased, unless special precautions are taken. These procedures, prior hereto, have involved a complete elimination of oxygen in the container for the active agent, and the use of laminar nitrogen flow during the process of filling the container with the combined local anaesthetic-adrenaline solution.

In the preferred embodiment, the vasoactive agent can be kept in a dry form, separated from the local anaesthetic (active compound), with the structure 618 sealed to keep the aqueous solution intact during storage and where the vasoactive agent is kept in its dry form, separated from the local anaesthetic solution during storage. The vasoactive agent is preferably kept in its dry form homogeneously distributed in a carrier material, e.g., cotton fiber, woven plastic thread and the like, with the same surface area as the first reservoir 615 containing the local anaesthetic (active compound).

Adrenaline in dry form, i.e., adrenaline thread which includes a cotton or woven plastic thread, impregnated with adrenaline in a pre-determine amount per unit length has been found to be suitable for use in the device of the present invention. The stability of the dry adrenaline present in this formulation has been found to be extremely favorable even when stored at room temperature for more than five years.

The gel contained in the first reservoir 615 and used for the electrolyte may also act as an adhesive, eliminating the need for the adhesive layer 648. In addition, a porous adhesive may be used.

The following formulations may be used in connection with the embodiment of the device 610 of the present invention illustrated in FIGS. 6A, 6B and 6C:

EXAMPLE 1

| | |
|---|---|
| Lidocaine hydrochloride monohydrate corresponding to lidocaine hydrochloride | 150 mg |
| Purified Water | 1 ml |

Lidocaine hydrochloride monohydrate is dissolved in purified water. The solution is adsorbed into a thin material of cellulose or plastic, such as Vetx® or Porex®.

EXAMPLE 2

| | |
|---|---|
| Ropivacaine hydrochloride monohydrate corresponding to ropivacaine hydrochloride | 35 mg |
| Purified Water | 1 ml |

Ropivacaine hydrochloride monohydrate is dissolved in purified water. The solution is adsorbed into a thin material of cellulose or plastic.

EXAMPLE 3

| | |
|---|---|
| Lidocaine hydrochloride monohydrate corresponding to lidocaine hydrochloride | 20 mg |
| Purified Water | 1 ml |

The preparation is prepared as with Example 2.

EXAMPLE 4

| | |
|---|---|
| Adrenaline base | 1.68 g |
| Hydrochloride acid | 5.04 ml |
| Sodium pyrosulfite | 0.10 g |
| Disodium tetracemin | 0.05 g |
| Purified Water | 100 g |

By varying the amount of water, solutions with different contents of vasoactive agent are obtained. The carrier material to be soaked with the vasoactive agent is of cotton thread, synthetic fibre or paper. The carrier material is soaked with the vasoactive solution and the solution is evaporated until the carrier is dry.

EXAMPLE 5

| | |
|---|---|
| Felypressin, Octapressin ® stock solution 25 IU/ml | 3.15 IU |
| Purified Water | 100 g |

By varying the amount of water, solutions with different contents of the peptide felypressin are obtained. The carrier material to be soaked with the peptide is of cotton thread, synthetic fiber or paper. The material is soaked with the peptide and the solution is evaporated until the carrier is dry.

In addition, peptides, such as felypressin have been found to be suitable. Preferably, both the active components, the local anaesthetic in its hydrochloride salt form or the peptide, and the vasoconstrictor (preferably adrenaline) are both easily soluble in aqueous solutions.

Thus, the various embodiments of the present invention can be used wherein at least one of the active compounds needs to be isolated. Drug, medication and active compound have been used herein to mean any pharmaceutical agent, such as therapeutic compounds, diagnostic agents and the like.

The particular matrix of the material or the method of manufacture is not essential to the present invention. For example, the drug can be spray-dried onto an inert support such as a non-woven material, a screen or scrim, or a variety of micro-porous supports such as nylon, polyethylene, and polypropylene. In addition, the drug can be dispersed in an ointment or liquid and cast and dried onto a support. Also the drug can be mixed with dispersing agents or water-soluble polymers and pressed into a dry wafer or pellets that dissolve rapidly in water. The drug can be uniformly dispersed in a de-hydrated gel that can be hydrated rapidly from an added source of water.

The particular source of water or mechanisms of hydration are not essential to the present invention and may include aqueous solution stored in a compartment adjacent to the dry-drug compartment or moisture from the body (due to occlusion of the application site) can supply the necessary hydration to the drug reservoir to dissolve the drug formulation. In addition, a towellette or moist pad in a separate pouch can be supplied along with the device and prior to attachment to the patient, the site of application and/or the drug reservoir can be moistened. Alternatively, moisture can be applied as a spray. The particular means is a matter of choice depending upon the formulation or state of the drug.

In addition, while the present invention has been described in connection with iontophoresis, it should be appreciated that it may be used in connection with other principles of active introduction, i.e., motive forces, such as electrophoresis which includes the movement of particles in an electric field toward one or other electric pole, anode, or cathode and electro-osmosis which includes the transport of uncharged compounds due to the bulk flow of water induced by an electric field. Also, it should be appreciated that the patient may include humans as well as animals.

While the preferred embodiments of the present invention has been described so as to enable one skilled in the art to practice the device of the present invention, it is to be understood that variations and modifications may be employed without departing from the concept and intent of the present invention as defined in the following claims. The preceding description is intended to be exemplary and should not be used to limit the scope of the invention. The scope of the invention should be determined only by reference to the following claims.

What is claimed is:

1. A user activated device for iontophoretically delivering at least one medication to an applied area of a patient, comprising:
    an electrode assembly means for driving a medication into the applied area of the patient;
    wherein the electrode assembly means is situated in electrical communication with a first reservoir, having an electrolyte;
    a second reservoir containing a substantially non-hydrated medication to be delivered to the applied area of the patient;
    a first holding means for holding the electrode assembly means and the first reservoir, said first holding means including a means for maintaining the electrode assembly means in electrical communication with the first reservoir; a second holding means for holding the second reservoir and including a means for maintaining the second reservoir separate in relation to the first reservoir; the first holding means and the second holding means each having a release liner or barrier for sealing the first holding means and the second holding means so that prior to activation the second reservoir containing the medication is isolated from the first reservoir and maintained in a non-hydrated condition to prevent degradation and dilution of the medication contained in the second reservoir;
    wherein the device is activated by removing the release liner or barrier and placing the first reservoir in contact with the second reservoir, thereby to at least partially hydrate the medication contained in the second reservoir and to bring the first reservoir and the second reservoir into electrical communication with one another.

2. The user activated device of claim 1, wherein the electrolyte is an electrically conductive gel.

3. The user activated device of claim 2, wherein said first holding means and said second holding means are hingedly connected together along a bendable member so that the device may be activated by folding the holding means along the bendable member to bring the first reservoir and the second reservoir into electrical communication.

4. The user activated device of claim 3, wherein said barrier means is adapted to include a pull tab extending from the holding means so that the device may be activated by pulling the tab to remove the barrier from the device to bring the first reservoir and the second reservoir into electrical communication.

5. The user activated device of claim 3, wherein said first reservoir includes a second medication to be delivered to the applied area of the patient.

6. The user activated device of claim 3, further comprising at least one barrier situated between the first reservoir and the second reservoir to limit the presence of competing ions when the two reservoirs are in electrical communication.

7. The user-activated device of claim 3, further comprising a flexible member which extends from the first holding means or the second holding means, said flexible member having a third reservoir attached thereto, said third reservoir containing a substantially non-hydrated second medication to be delivered to the applied area of the patient; the third reservoir having a release liner or barrier for sealing the third reservoir so that prior to activation, the third reservoir is isolated from the first reservoir and maintained in a non-hydrated condition to prevent degradation and dilution of the medication contained in the third reservoir; the third reservoir may be activated by removing the release liner or barrier and folding the flexible member so that the third reservoir is at least partially hydrated and placed in electrical communication with second reservoir after the second reservoir has been placed in electrical communication with the first reservoir.

8. A user activated device for iontophoretically delivering at least two medications through an applied area of a patient, comprising:
    an electrode assembly means for driving a medication into the applied area of the patient to be absorbed by the body of the patient;
    wherein the electrode assembly means is situated in electrical communication with a first reservoir, which contains a substantially hydrated electrolyte and an active compound to be delivered to the applied area of the patient;
    a second reservoir containing a substantially non-hydrated vasoactive agent medication to be delivered to the applied area of the patient;
    a first holding means for holding the electrode assembly means and the first reservoir, said first holding means including a means for maintaining the electrode assembly means in electrical communication with the first reservoir; a second holding means for holding the second reservoir and including a means for maintaining the second reservoir separate in relation to the first reservoir; the first holding means and the second holding means each having a release liner or barrier for sealing the first holding means and the second holding means so that prior to activation the second reservoir containing the medication is isolated from the first reservoir and maintained in a non-hydrated condition to prevent degradation and dilution of the medication contained in the second reservoir;
    wherein the device is activated by removing the release liner and placing the first reservoir in contact with the second reservoir, thereby to at least partially hydrate the vaso active agent contained in the second reservoir and to bring the first reservoir and the second reservoir into electrical communication with one another.

9. The user activated device of claim 8, wherein the electrolyte is an electrically conductive gel.

10. The user activated device of claim 9, wherein the active compound is a local anesthetic and the vasoactive agent is a vaso-constricting compound.

11. The user activated device of claim 10, wherein the local anesthetic is lidocaine and the vaso-constricting compound is adrenaline.

* * * * *